United States Patent [19]

Saunders et al.

[11] Patent Number: 5,173,487
[45] Date of Patent: Dec. 22, 1992

[54] MEVINIC ACID DERIVATIVES

[75] Inventors: Jeffrey O. Saunders, Somerville, Mass.; Eric M. Gordon, Pennington, N.J.

[73] Assignee: E. R. Squibb & Sons, Inc., Princeton, N.J.

[21] Appl. No.: 435,843

[22] Filed: Nov. 13, 1989

[51] Int. Cl.$^5$ .................... A61K 31/365; C07C 69/74; C07D 309/30

[52] U.S. Cl. ................... 514/227.5; 514/548; 514/529; 514/460; 514/227.8; 514/231.5; 514/237.5; 514/255; 514/315; 514/330; 514/354; 514/397; 514/400; 514/422; 514/423; 549/292; 560/119; 560/256; 548/517; 548/535; 548/311.1; 548/338.1; 546/221; 546/268; 546/326; 544/374; 544/149; 544/172; 544/60; 544/59

[58] Field of Search ............... 560/119, 256; 514/529, 514/824, 460, 548, 227.5; 549/292

[56] References Cited

U.S. PATENT DOCUMENTS

| | | | |
|---|---|---|---|
| 3,983,140 | 9/1976 | Endo et al. | 260/343.5 |
| 4,049,495 | 9/1977 | Endo et al. | 195/36 |
| 4,231,938 | 11/1980 | Monaghan et al. | 260/343.5 |
| 4,346,227 | 8/1982 | Terahara et al. | 560/119 |
| 4,410,629 | 10/1983 | Terahara et al. | 435/146 |
| 4,444,784 | 4/1984 | Hoffman et al. | 424/279 |
| 4,448,979 | 5/1984 | Terahara et al. | 549/292 |
| 4,450,171 | 5/1984 | Hoffman et al. | 424/279 |
| 4,866,090 | 9/1989 | Hoffman et al. | 560/119 |

FOREIGN PATENT DOCUMENTS 0065835 12/1982 European Pat. Off. .

OTHER PUBLICATIONS

Terohara et al. "M-4 and iso M-4 derviatives and compositions containing them" CA 98 215415y (1983).
F. M. Singer et al., "New Inhibitors of in vitro Conversion of Acetate and Mevalonate to Cholesterol", Proc. Soc. Exper. Biol. Med., 102, 370 (1959).
F. H. Hulcher, "Inhibition of Hepatic Cholesterol Biosynthesis by 3,5-Dihydroxy—3,4,4-trimethylvaleric Acid and its Site of Action," Arch. Biochem. Biophys., 146, 422 (1971).
A. G. Brown et al., "Crystal and Molecular Structure of Compactin, a New Antifungal Metabolite from Penicillium Brevicompactum", J. Chem. Soc. Perkin I. 1165–1170 (1976).

Primary Examiner—C. Warren Ivy
Assistant Examiner—Amelia A. Owens
Attorney, Agent, or Firm—Timothy J. Gaul

[57] ABSTRACT

Antihypercholesterolemic activity, due to competitive inhibition of HMG CoA reductase, is exhibited by a compound of the formula

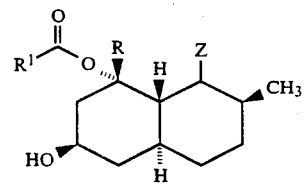

wherein:

Z is 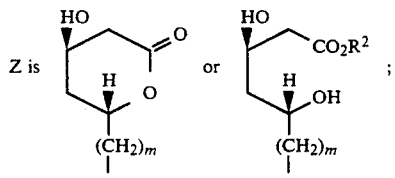

m is 0 to 3;
R is selected from:
  (1) alkyl;
  (2) substituted alkyl;
  (3) alkoxy;
  (4) alkenyl;
  (5) cycloalkyl;
  (6) phenyl; and
  (7) substituted aryl; and
$R^1$ and $R^2$ are as defined in the specification.

12 Claims, No Drawings

MEVINIC ACID DERIVATIVES

FIELD OF THE INVENTION

The present invention relates to mevinic acid derivatives that inhibit 3-hydroxy-3-methylglutaryl coenzyme A (HMG CoA) reductase, an enzyme used in cholesterol biosynthesis. The compounds of this invention are, therefore, useful as antihypercholesterolemic agents.

BACKGROUND OF THE INVENTION

F. M. Singer et al., "New Inhibitors of in vitro Conversion of Acetate and Mevalonate to Cholesterol", *Proc. Soc. Exper. Biol. Med.*, 102, 370 (1959) and F. H. Hulcher, "Inhibition of Hepatic Cholesterol Biosynthesis by 3,5-Dihydroxy-3,4,4,-trimethylvaleric Acid and its Site of Action," *Arch. Biochem. Biophys.*, 146, 422 (1971) disclose that certain mevalonate derivatives inhibit the biosynthesis of cholesterol.

Singer et al. reported that fluoromevalonic acid is more effective in inhibiting biosynthesis of cholesterol (as measured by in vitro conversion of labeled acetate and labeled mevalonate into cholesterol) than Δ4-androstene-17α-ol-3-one-17β-oic acid and Δ1-testololactone.

Hulcher reported that an analog of mevalonic acid (3,5-dihydroxy-3,4,4-trimethylvaleric acid) strongly inhibits cholesterol biosynthesis by rat liver homogenates.

U.S. Pat. No. 3,983,140 to Endo et al. discloses the fermentation product ML-236B, referred to generically as compactin and mevastatin, which has the structure

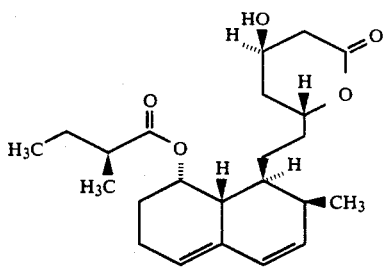

A

This compound is prepared by cultivation of a microorganism of the genus Penicillium. The fermentation process is disclosed in U.S. Pat. No. 4,049,495 issued Sep. 20, 1977 to Endo et al.

Brown, A. G., et al., (Beecham Pharmaceuticals Research Div.), "Crystal and Molecular Structure of Compactin, a New Antifungal Metabolite from Penicillium Brevicompactum", *J. Chem. Soc. Perkin I.* 1165–1170 (1976) confirms that compactin has the complex mevalonolactone structure disclosed by Endo et al. in the above patents.

U.S. Pat. No. 4,231,938 to Monaghan et al. discloses mevinolin (also called lovastatin, Monacolin K, and MK-803), which has the structure

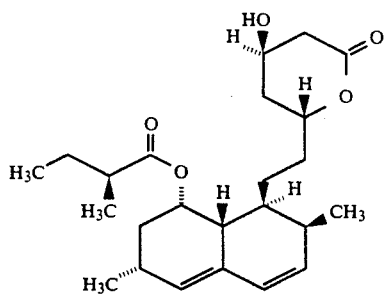

B

This compound is prepared by culturing a microorganism of the genus *Aspergillus*.

U.S. Pat. No. 4,346,227 to Terahara et al. discloses pravastatin, which has the structure

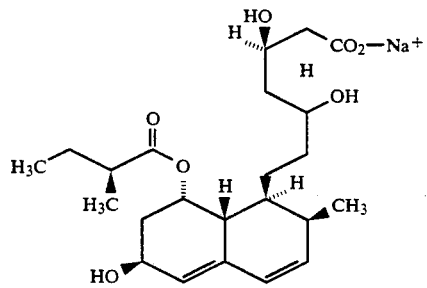

Pravastatin is prepared by the enzymatic hydroxylation of compactin or its carboxylic acid, as disclosed in U.S. Pat. No. 4,410,629 to Terahara et al.

U.S. Pat. No. 4,448,979, issued May 15, 1984 to Terahara et al., discloses the lactone of pravastatin.

U.S. Pat. Nos. 4,444,784 and 4,450,171 to Hoffman et al disclose various antihypercholesterolemic compounds, including synvinolin (simvastatin), which has the structure

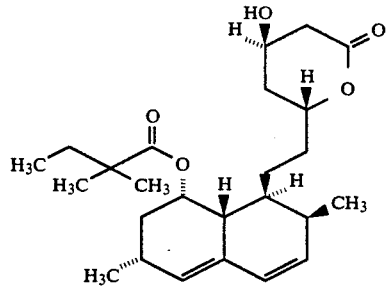

D

The Hoffman patents further disclose compounds of the structures

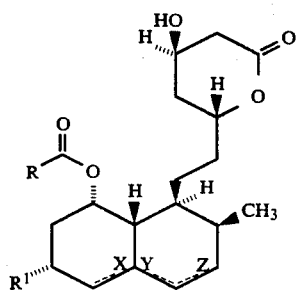

E

-continued
and

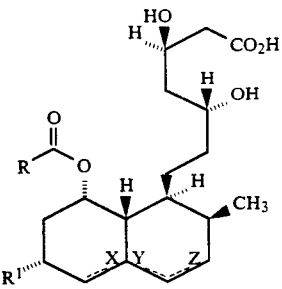
F wherein R¹ is H or CH₃, R can be an alkyl group including

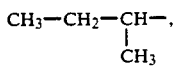

X, Y and Z are single and/or double bonds in all possible combinations.

European Patent Application 0065835A1, filed by Sankyo, discloses cholesterol biosynthesis-inhibiting compounds of the structure

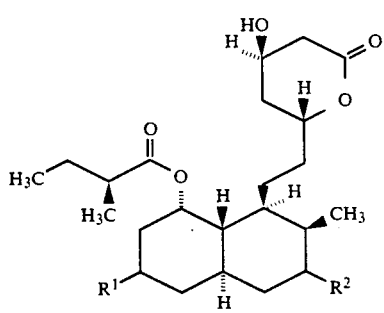
G

The same application discloses the corresponding free carboxylic acids, which may be represented by the formula

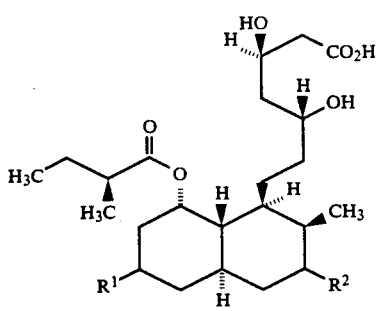
H in which one of R¹ and R² represents a hydrogen atom and the other represents a hydroxy group. The Sankyo application further discloses salts and esters of the carboxylic acids.

SUMMARY OF THE INVENTION

Antihypercholesterolemic activity is exhibited by compounds of the formula

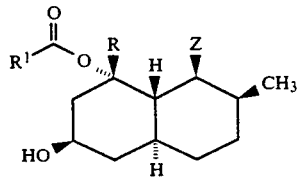

wherein, in formula I and throughout this specification hereinafter, the above symbols are defined as follows:

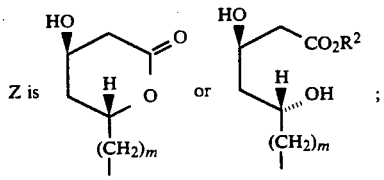

R is selected from:
(1) alkyl;
(2) substituted alkyl in which one or more substituents are selected from
  (a) hydroxyl,
  (b) alkoxy,
  (c) alkoxycarbonyl,
  (d) acyloxy,
  (e) cycloalkyl,
  (f) aryl,
  (g) substituted aryl having substituents X and Y, and
  (h) oxo;
(3) alkoxy;
(4) alkenyl;
(5) cycloalkyl;
(6) aryl; and
(7) substituted aryl having substituents X and Y;
R¹ is selected from:
(1) alkyl;
(2) substituted alkyl in which one or more substituents are selected from
  (a) halogen,
  (b) hydroxyl,
  (c) alkoxy,
  (d) alkoxycarbony,
  (e) acyloxy,
  (f) cycloalkyl,
  (g) aryl,
  (h) substituted aryl having substituents X and Y,
  (i) alkyl—S(O)$_n$,
  (j) cycloalkyl—S(O)$_n$,
  (k) aryl—S(O)$_n$,
  (l) substituted aryl—S(O)$_n$ having substituents X and Y, and
  (m) oxo;
(3) alkoxy;
(4) alkenyl;
(5) cycloalkyl;
(6) substituted cycloalkyl having one or more substituents selected from
  (a) alkyl,
  (b) substituted alkyl having a substituent selected form
    (i) halogen,
    (ii) hydroxy,
    (iii) alkoxy, (iv) alkoxycarbonyl,
(v) acyloxy,
(vi) aryl,
(vii) substituted aryl having substituents
(viii) alkyl—S(O)$_n$,
(ix) cycloalkyl—S(O)$_n$,
(x) aryl—S(O)$_n$,
(xi) substituted aryl—S(O)$_n$ having substituents X and Y, and
(xii) oxo,
(c) alkyl—S(O)$_n$,
(d) cycloalkyl—S(O)$_n$,
(e) aryl—S(O)$_n$,
(f) substituted aryl—S(O)$_n$ having substituents X and Y,
(g) halogen,
(h) hydroxy,
(i) alkoxy,
(j) alkoxycarbonyl,
(k) acyloxy,
(l) aryl, and
(m) substituted aryl having substituents X and Y;
(7) aryl;
(8) substituted aryl having substituents X and Y;
(9) amino;
(10) alkylamino;
(11) dialkylamino;
(12) arylamino;
(13) substituted arylamino having substituents X and Y;
(14) alkyl(substituted aryl)amino having substituents X and Y;
(15) diarylalkylamino;
(16) substituted arylalkylamino having substituents X and Y;
(17) a member selected from
(a) piperidinyl,
(b) pyrrolidinyl,
(c) piperazinyl,
(d) morpholinyl,
(e) thiomorpholino,
(f) histaminyl,
(g) 3-aminomethyl pyridinyl; and
(18) hydroxy substituted alkylamine;
$R^2$ is selected from:
1) hydrogen;
(2) ammonium;
(3) alkali metal, such as lithium, sodium or potassium;
(4) alkyl;
(5) alkyl substituted with phenyl;
(6) dialkylamine;
(7) alkylarylamine; and
(8) diarylalkylamine;
X and Y are independently hydrogen, halogen, trifluoromethyl, alkyl, nitro, alkoxy, or cyano;
m is an integer from 0 to 3; and
n is 0, 1, or 2.

Formula I compounds provide hypocholesterolemic activity by competitive inhibition of HMG CoA reductase, a key enzyme in cholesterol biosynthesis. These compounds exhibit such activity while maintaining chemical and metabolic stability.

DESCRIPTION OF THE INVENTION

Definition of Terms

Listed below are definitions of various terms used to describe this invention. These definitions apply to the terms as they are used throughout the specification (unless otherwise limited in specific instances) either individually or as part of a larger group. Where exemplary and preferred groups are listed in any definition of a term, these groups are used to illustrate rather than limit the meaning of the term.

The term "alkali metal" refers to lithium, sodium, and potassium.

The term "lower alkyl" or "alkyl" as employed herein by itself or as part of another group includes both straight and branched chain hydrocarbon groups, such as methyl, ethyl, propyl, isopropyl, butyl, t-butyl, isobutyl, pentyl, isopentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like. For $R_2$, alkyl groups having 1 to 5 carbons are preferred. For X and Y, alkyl groups having 1 to 3 carbons are preferred. In all other instances, alkyl groups having 1 to 10 carbons are preferred.

The term "cycloalkyl" by itself or as part of another group includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl.

The term "alkenyl" by itself or as part of another group refers to both straight and branched chain hydrocarbon groups having one or more double bonds. Those groups having 2 to 10 carbon atoms are preferred. The term "alkenyl" further includes groups having one or two halo substituents, an alkoxy substituent, an aryl substituent, an alkyl-aryl substituent, a haloaryl substituent, a cycloalkyl substituent, or an alkylcycloalkyl substituent.

The terms "halogen" and "halo" refer to fluorine, chlorine, bromine and iodine.

The term "aryl" as employed herein by itself or as part of another group refers to monocyclic or bicyclic aromatic groups containing either 6 or 10 carbons in each group, such as phenyl or naphthyl, respectively.

The term "aralkyl", "arylalkyl", "alkylaryl" or "aryl-lower alkyl" as used herein by itself or as part of another group refers to lower alkyl groups as discussed above having an aryl substituent, such as phenyl. Groups having up to 10 carbons in the alkyl substituent are preferred.

The term "alkoxy" refers to a lower alkyl group linked to an oxygen atom. Alkoxy groups having 1 to 10 carbons are preferred.

The term "acyl" includes all organic moieties that may be derived from an organic acid (i.e., a carboxylic acid) by exchange of the hydroxyl group.

Exemplary acyl groups are:

(a) Aliphatic groups having the formula

wherein $R^5$ is alkyl, cycloalkyl, alkoxy, alkenyl, cycloalkenyl, cyclohexadienyl, or alkyl or alkenyl substituted with one or more halogen, cyano, nitro, amino, mercapto, alkylthio, or cyanomethylthio groups.

(b) Carbocyclic aromatic groups having the formula

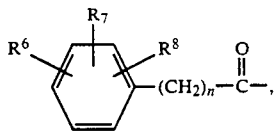

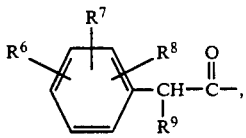

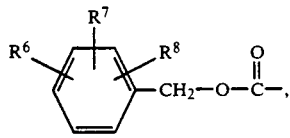

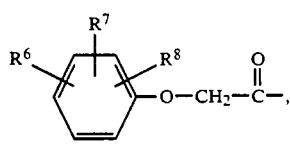

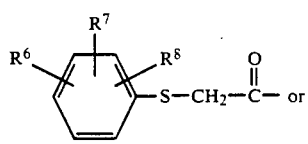

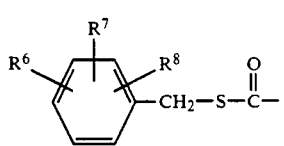

wherein n is 0, 1, 2 or 3; $R^6$, $R^7$, and $R^8$ are independently hydrogen, halogen, hydroxyl, nitro, amino, cyano, trifluoromethyl, alkyl of 1 to 4 carbon atoms, alkyloxy of 1 to 4 carbon atoms or aminomethyl; and $R^9$ is amino, hydroxyl, a carboxyl salt, protected carboxyl, formyloxy, a sulfo salt, a sulfoamino salt, azido, halogen, hydrazino, alkylhydrazino, phenylhydrazino, or [(alkylthio)thioxomethyl]thio.

(c) Heteroaromatic groups having the formula

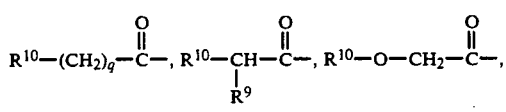

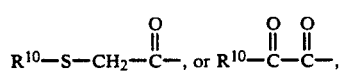

wherein q is 0, 1, 2 or 3; $R^9$ is as defined above; and $R^{10}$ is a substituted or unsubstituted 5-, 6- or 7-membered heterocyclic ring containing 1, 2, 3 or 4 (preferably 1 or 2) nitrogen, oxygen and sulfur atoms. Exemplary heterocyclic rings are thienyl, furyl, pyrrolyl, pyridinyl, pyrazolyl, pyrazinyl, thiazolyl, pyrimidinyl and tetrazolyl. Exemplary substituents are halogen, hydroxyl, nitro, amino, cyano, trifluoromethyl, alkyl of 1 to 4 carbon atoms, alkoxy of 1 to 4 carbon atoms, or

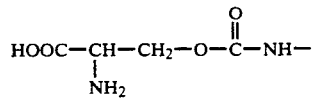

(d) [[(4-Substituted-2,3-dioxo-1-piperazinyl)carbonyl]amino]arylacetyl groups having the formula

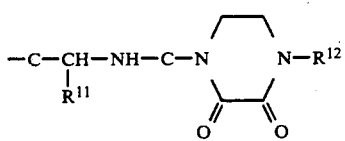

wherein $R^{11}$ is an aromatic group (including carbocyclic aromatics such as those of the formula

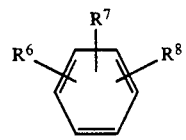

and heteroaromatics as included within the definition of $R^{10}$); and $R^{12}$ is alkyl, substituted alkyl (wherein the alkyl group is substituted with one or more halogen, cyano, nitro, amino or mercapto groups), arylmethyleneamino (i.e., $-N=CH-R^{11}$ wherein $R^{11}$ is as defined above), arylcarbonylamino (i.e.,

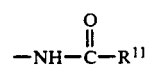

wherein $R^{11}$ is as defined above) or alkylcarbonylamino.

(e) (Substituted oxyimino)arylacetyl groups having the formula

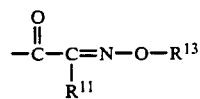

wherein $R^{11}$ is as defined above and $R_{13}$ is hydrogen, alkyl, cycloalkyl, alkylaminocarbonyl, arylaminocarbonyl (i.e.,

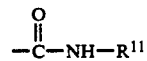

where $R^{11}$ is as defined above) or substituted alkyl (wherein the alkyl group is substituted with 1 or more halogen, cyano, nitro, amino, mercapto, alkylthio, aromatic group (as defined by $R^{11}$), carboxyl (including salts thereof, amido, alkoxycarbonyl, phenylmethoxycarbonyl, diphenylmethoxycarbonyl, hydroxyalkoxyphosphinyl, dihydroxyphosphinyl, hydroxy (phenylmethoxy)phosphinyl, or dialkoxyphosphinyl substituents).

(f) (Acylamino)arylacetyl groups having the formula $$-\overset{O}{\overset{\|}{C}}-\underset{\underset{R^{11}}{|}}{CH}-NH-\overset{O}{\overset{\|}{C}}-R^{14}$$

wherein $R^{11}$ is as defined above and $R^{14}$ is

[structure: substituted aryl with $R^6, R^7, R^8$ and $-(CH^2)_n-O-$]

amino, alkylamino, (cyanoalkyl)amino, amido, alkylamido, (cyanoalkyl)amido, $$-CH_2-NH-\overset{NH}{\overset{\|}{C}}-\langle\rangle, \quad \langle N \rangle-\overset{NH_2}{\underset{|}{CH}}-CH_2-\overset{O}{\overset{\|}{C}}-NH-CH_3,$$

[pyridinol-phenyl-SO$_2$-N(CH$_2$-CH$_2$-OH)$_2$ structure]

[HO-pyridine-CH$_3$ structure], [OH-naphthyridine structure], or

[OH-pyridopyrimidine-piperazine-CHO structure]

(g) [[[3-Substituted-2-oxo-1-imidazolidinyl]carbonyl-]amino]arylacetyl groups having the formula $$-\overset{O}{\overset{\|}{C}}-\underset{\underset{R^{11}}{|}}{CH}-NH-\overset{O}{\overset{\|}{C}}-\underset{\underset{CH_2-CH_2}{|}}{N}\overset{\overset{O}{\overset{\|}{C}}}{}N-R^{15}$$

wherein $R^{11}$ is as defined above and $R^{15}$ is hydrogen, alkylsulfonyl, arylmethyleneamino (i.e., $-N=CH-R^{11}$ wherein $R^{11}$ is as defined above), $$-\overset{O}{\overset{\|}{C}}-R^{16}$$

(wherein in $R^{16}$ is hydrogen, alkyl or halogen substituted alkyl), aromatic group (as defined by $R^{11}$ above), alkyl or substituted alkyl (wherein the alkyl group is substituted with one or more halogen, cyano, nitro, amino or mercapto groups).

The term "alkoxycarbonyl" refers to alkoxy groups linked to —C=O. Groups having up to 10 carbon atoms are preferred.

The term "acyloxy" refers to acyl groups linked to one or more oxygen atoms. Groups having up to five carbon atoms are preferred.

The terms "alkylamine" and "alkylamino" refer to primary, second and tertiary amine groups having one or more alkyl substituents. Groups having up to five carbon atoms are preferred.

The term "arylamino" refers to primary, secondary, and tertiary amines having one or more aryl substituents.

The term "arylalkylamino" refers to primary, secondary, and tertiary amine groups having one or more arylalkyl substituents. Such groups having 1 to 10 carbons in the alkyl portion are preferred.

Preferred Moieties

The following moieties are preferred for the associated symbols:

R is alkyl or alkenyl;
$R^1$ is alkyl (preferably branched alkyl);
$R^2$ is alkali metal; and
m is 2.

The following moieties are most preferred for the associated symbols:

R is methyl or propenyl;
$R^1$ is 1,1-dimethylpropyl; and
$R^2$ is sodium.

Process of Preparation

The compound of this invention may be prepared by the following exemplary process, a portion of which, as indicated below, represents novel methodology.

Preparation of the compound of the formula

[Structure II: decalin-lactone compound with HO, H$_3$C, CH$_3$ substituents]  II is described in U.S. Pat. Nos. 3,983,140 and 4,346,227. In the process of forming compound I, compound II may be placed in an inert solvent (e.g., tetrahydrofuran or dichloromethane) under an inert atmosphere (e.g., argon or nitrogen) at a temperature of about 15° to 25° C. and treated with an appropriate silyl protecting agent (e.g., t-butyldimethylsilyl chloride, triethylsilyl chloride, phenyldimethylsilyl chloride or t-butyldiphenylsilyl chloride) in the presence of an appropriate amine base (e.g., imidazole, dimethylaminopyridine, or diisopropylethyl amine), resulting in a compound of the formula

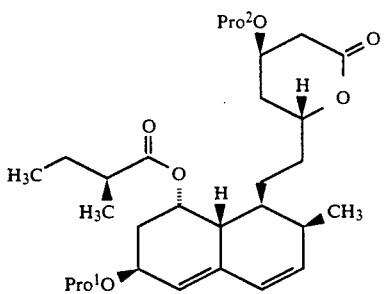

III wherein Pro¹ and Pro² are hydroxyl-protecting groups such as

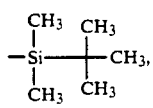

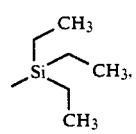

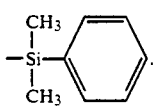

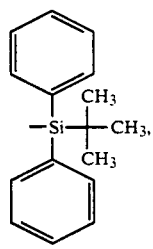

and the like.

Compound III, in turn, may be hydrogenated in an organic solvent (e.g., ethyl acetate) in the presence of a catalyst (e.g., platinum on activated carbon) to yield a compound of the formula

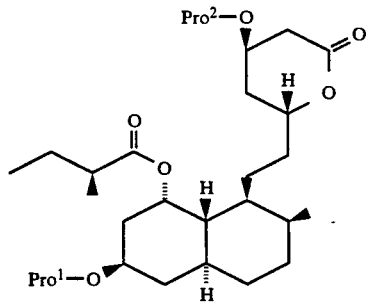

IV

Compound IV may be treated with a hydride reducing agent, such as diisobutylaluminum hydride (DIBAL), under an inert atmosphere (e.g., argon) at about −78° C. in an organic solvent (e.g., tetrahydrofuran) to yield a compound of the formula

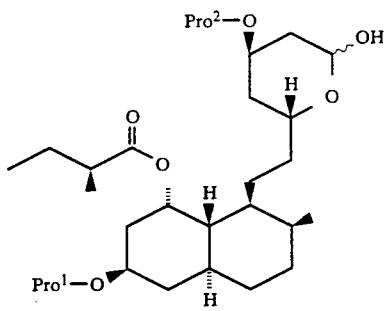

V

An appropriate vinyl ether (e.g., 2 methoxypropene) may be added to a solution of compound V, followed by treatment with an acid catalyst such as pyridinium p-toluene sulfonate (PPTS) in an organic solvent (e.g., methylene chloride) at about 0° C. under an inert atmosphere (e.g., argon). The result is a compound of the formula

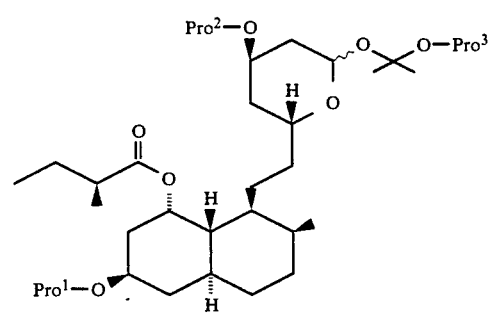

VI wherein Pro³ is an alkyl group, such as methyl.

Compound VI then may be added to a hydride reducing agent (e.g., lithium aluminum hydride) in an organic solvent (e.g., diethyl ether) at about ambient temperature under an inert atmosphere (e.g., argon) to yield the compound

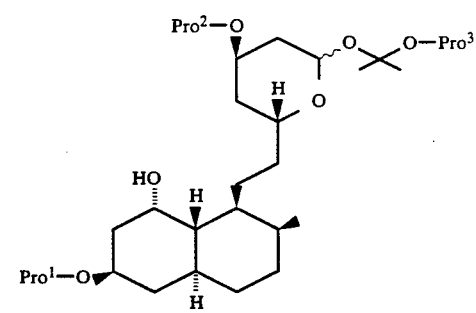

VII

The chemistry for the following conversions is considered to be novel:

VII→VIII→IX→X→XI.

Compound VII may be added to a solution of an appropriate mild oxidizing agent (e.g., Dess Martin periodinane) in an organic solvent (e.g., methylene chloride) to yield a compound of the formula

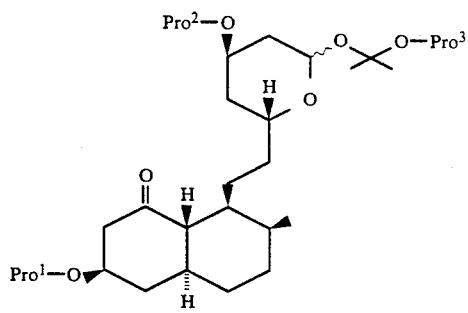

VIII

The decalone compound VIII may be placed in an organic solvent (e.g., tetrahydrofuran) under an inert atmosphere and treated with a Grignard reagent (e.g., methyl magnesium bromide) at about −78° C. to 0° C., with subsequent warming to room temperature. The result is a compound of the formula

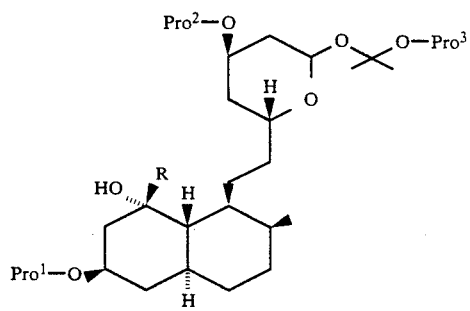

IX

Compound IX may be placed in an organic solvent (e.g., tetrahydrofuran) and treated with a mild, aqueous acid solution to yield

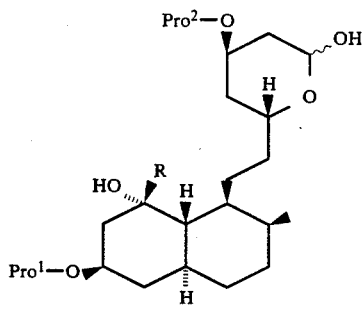

X

Compound X, in turn may be placed in an appropriate solvent such as acetone and oxidized under mild, neutral conditions by treatment with a catalytic oxidant (e.g., tris(triphenylphosphine) ruthenium (II) chloride) and a re-oxidant (e.g., N-methylmorpholine-N-oxide) in the presence of 4Å molecular sieves, to yield

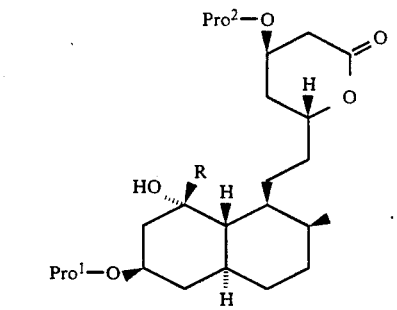

XI

Compound XI may be added to a mixture of an anhydrous inorganic bromide source (e.g., lithium bromide), an acylating agent (e.g., 2,2-dimethylbutyryl chloride) and a catalyst (e.g. dimethylaminopyridine) in a solvent such as anhydrous pyridine, yielding

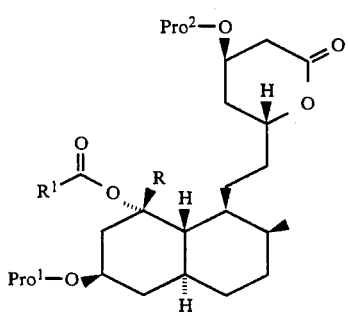

XII

A desilylating agent such as HF-pyridine complex may be added to a solution of compound XII in an organic solvent (e.g., methyl cyanide) at a temperature of about 0° to 25° C. to yield

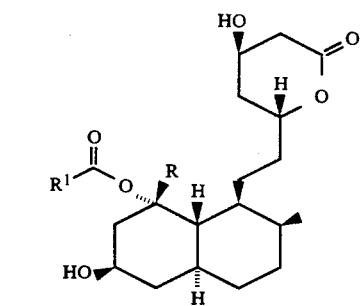

IA

Compound IA, in turn, may be placed in such solvents as dioxane and water and treated with a base (e.g., sodium hydroxide) to yield

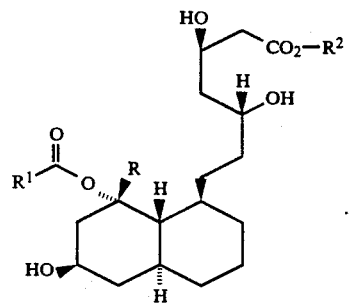

IB

Compounds IA and IB are within formula I.

Use and Utility

The compound of formula I of the invention can be formulated with a pharmaceutical vehicle or diluent. The pharmaceutical composition can be formulated in a classical manner utilizing solid or liquid vehicles or diluents and pharmaceutical additives of a type appropriate to the desired mode of administration. The compounds can be administered by an oral route in the form of tablets, capsules, granules or powders, for example, or by a parental route in the form of injectable preparations.

A typical capsule for oral administration contains active ingredients (25 mg), lactose (75 mg) and magnesium stearate (15 mg). This mixture is passed through a 60-mesh sieve and packed into a No. 1 gelatin capsule.

A typical injectable preparation is produced by asceptically placing 25 mg of a water soluble salt of sterile active ingredient into a vial, then asceptically freeze-drying and sealing the vial. For use, the contents of the vial are mixed with 2 ml of physiological saline, to produce an injectable preparation.

The compounds of the invention inhibit HMG CoA reductase and, therefore, cholesterol biosynthesis. Such compounds are useful in treating:

(1) atherosclerosis (to inhibit progression of disease),
(2) hyperlipidemia (to inhibit development of atherosclerosis), and
(3) nephrotic hyperlipidemia.

In addition, the compounds of the invention increase plasma high-density lipoprotein cholesterol levels.

As HMG CoA reductase inhibitors, the compounds of the invention may also be useful in inhibiting formation of gallstones and in treating tumors. In addition, the compounds of the invention may be useful in elevating high density lipid (HDL) cholesterol levels while lowering low density lipid (LDL) cholesterol and serum triglyceride levels.

The compounds of the invention may also be employed in combination with:

(1) an antihyperlipoproteinemic agent (e.g., probucol),
(2) one or more serum cholesterol-lowering agents (e.g., "Lopid" ®, or gemfibrozil),
(3) bile acid sequestrants (e.g., cholestyramine,
(4) colestipol,
(5) DEAE-Sephadex
(6) clofibrate,
(7) nicotinic acid and its derivatives,
(8) neomycin,
(9) p-aminosalicyclic acid,
(10) lovastatin, pravastatin, visinolin (velostatin, symvastatin or sinvinolin) and the like, and
(11) one or more squalene synthetase inhibitors.

The above compounds to be employed in combination with the invention will be used in amounts indicated in the Physicians' Desk Reference (PDR).

The dose to be administered depends on the unitary dose, the symptoms, and the age and body weight of the patient. A dose for adults is preferably between 20 and 2,000 mg per day, which can be administered in a single dose or in one to four doses per day.

The compounds of this invention also have useful antifungal activities. For example, they may be used to control strains of *Penicillium sp., Aspergillus niger, Cladosporium sp., Cochliobolus miyabeorus* and *Helminthosporium cynodnotis*. For those utilities, they are first admixed with suitable formulating agents, powders, emulsifying agents or such solvents as aqueous ethanol, and then sprayed or dusted on the plants to be protected.

Preferred Embodiments

The following working examples represent preferred embodiments of the invention. Unless otherwise specified, all temperatures are in degrees Celsius (° C.).

EXAMPLE 1

[1S-[1α, 3β, 7β, 8β(2S* 4S*) 8a β]-2
2-Dimethylbutanoic acid,
decahydro-3-hydroxy-1,7-dimethyl-8-[2-(tetrahydro-4-hydroxy-6-oxo-2H-pyran-2-yl)-ethyl]-1-naphthalenyl
ester 1-A. [1S-[1α(R*),3β,7β,8β(2S*,4S*),8a,β]-2-Methylbutanoic acid, 1,2,3,7,8,8a-hexahydro-3-[[(1,1-dimethylethyl)dimethylsilyl]oxy]-7-methyl-8-[2-(tetrahydro-4-[[(1,1-dimethylethyl)dimethylsilyl]oxy]-6-oxo-2H-pyran-2-yl)ethyl]-1-naphthalenyl ester The starting material for preparation of intermediate A was [1S-[1α(R*), 3β,4β,7β,8β(2S*, 4S*), 8aβ] -2-methylbutanoic acid, 3-hydroxy-1,2,3,7,8,8a-hexahydro-7-methyl-8-[2-(tetrahydro-4-hydroxy-6-oxo-2H-pyran-2-yl)ethyl]-1-naphthalenyl ester. Preparation of this starting material has been described in U.S. Pat. Nos. 3,983,140 and 4,346,227.

A slurry of 21.7 g (0.0535 mol) of the starting material in 50 mL of dry methylene chloride was treated with 5.5 g (0.374 mol, 7.0 eq) of imidazole, followed by 26.6 g (0.176 mol, 3.3 eq) of t-butyl-dimethylsilylchloride. After stirring for 15 hours at ambient temperature under argon, the reaction mixture was filtered and concentrated. The residue was dissolved in ethyl acetate, filtered again, and concentrated. The purified product was isolated by filtration through silica gel, eluting with 25% hexanes in ethyl acetate followed by 10% hexanes in ethyl acetate, in a yield of 30.3 g (89%) as a colorless, viscous oil.

Thin layer chromatography: $R_f$=0.23 (silica gel, 20% ethyl acetate in hexanes).

1-B. [1S-[1α(R*),3β,4aα,7β,8β(2S*,4S*),8a,β]-2-Methylbutanoic acid, decahydro-3-[[(1,1-dimethylethyl)dimethylsilyl]oxy]-7-methyl-8-[2-(tetrahydro-4-[[(1,1-dimethylethyl)dimethylsilyl]oxy]-6-oxo-2H-pyran-2-yl)ethyl]-1-naphthalenyl ester A solution of 30.3 g (0.0477 mol) of intermediate 1-A in ca. 250 mL of ethyl acetate was thoroughly degassed and purged with argon. Two large scoops of platinum on carbon (Pt-C) were added, and the resultant mixture was subjected to 50 psi of $H_2$ on a parr apparatus overnight (18 hours). An aliquot of the reaction mixture was treated with HF, and analysis of this by thin layer chromatography indicated that the reaction was incomplete. The reaction mixture was filtered through Celite ®, treated with two scoops of Pt-C, and resubjected to $H_2$ (50 psi) on the parr apparatus for an additional 20 hours. At this time, analysis by thin layer chromatography indicated complete reaction with generation of the desired product and desilyated products. The mixture was filtered through Celite ®, and the filtrate was concentrated in vacuo. The residue was dissolved in ca. 150 mL of methylene chloride and treated with 4.87 g (0.0716 mol, 1.5 eq) of imidazole and 9.34 g (0.0620 mol, 1.3 eq) of t-butyl-dimethyl-silylchloride. After stirring for 3 hours, the reaction mixture was concentrated, diluted with ethyl acetate, filtered, and concentrated.

The crude product was purified by chromatography on silica gel, eluting with 25% ethyl acetate in hexanes to give 30.2 g (99%) of intermediate 1-B as a colorless, viscous oil. Thin layer chromatography: $R_f = 0.25$ (silica gel, 20% ethyl acetate in hexanes).

1-C. [1S-[1α(R*), 3β,4aα,7β,8β(2S*,4S*),8a,β]-2-Methylbutanoic acid, decahydro-3-[[(1,1-dimethylethyl)dimethylsilyl]oxy]-7-methyl-8-[2-(tetrahydro-4-[[(1,1-dimethylethyl)dimethylsilyl]oxy]-6-hydroxy-2H-pyran-2-yl)ethyl]-1-naphthalenyl ester A solution of 983 mg (1.54 mmol) of intermediate 1-B in 25 mL tetrahydrofuran was treated with diisobutylaluminum hydride (1.69 mmol, 1.13 mL of a 1.5 M solution in toluene) in a dropwise fashion via a syringe under argon at −78° C. After stirring for 2 hours at −78° C., methanol (0.27 mL) was added, and the solution was stirred for 10 minutes. The cooling bath was removed, and then water (1.1 mL), Celite® (1.1 g), and sodium sulfate (5.5 g) were added. This mixture was stirred for 1 hour and then filtered. The filtrate was concentrated to give 0.983 g (100%) of a colorless oil which was used directly in the subsequent reaction without further purification. A portion of the crude material was chromatographed on silica gel, eluting with 1% isopropyl alcohol in hexanes. $^1$H NMR showed lactol isomers and trace amounts of starting material. Thin layer chromatography: $R_f = 0.22–0.39$ (silica gel, 20% ethyl acetate in hexanes).

1-D. [1S-[1α(R*),3β,4aα,7β,8β(2S*,4S*),8a,β]-2-Methylbutanoic acid, decahydro-3-[[(1,1-dimethylethyl)dimethylsilyl]oxy]-7-methyl-8-[2-(tetrahydro-4-[[(1,1-dimethylethyl)dimethylsilyl]oxy]-6-(1-methoxy-1-methylethoxy)-2H-pyran-2-yl)ethyl]-1-naphthalenyl ester To a solution of 881 mg (1.37 mmol) of crude intermediate 1-C in 15 mL methylene chloride at 0° C. under argon was added 1.97 mL (20.6 mmol, 15 eq) of 2-methoxypropene, followed by a solution of 21 mg (0.0825 mmol, 0.06 eq) of pyridinium p-toluene sulfonate (PPTS) in 2 mL methylene chloride. After stirring the mixture for 3 hours, the homogeneous reaction mixture was poured into aqueous sodium hydrogen carbonate and diluted with ethyl acetate. The aqueous layer was extracted with ethyl acetate (twice), and the combined organic layers were dried (magnesium sulfate), concentrated, and chromatographed on silica gel, eluting with 5% ethyl acetate in hexanes followed by 25% ethyl acetate in hexanes.

A higher $R_f$ impurity was present in some of the fractions containing intermediate 1-D. These fractions were combined, concentrated, and rechromatographed on silica gel, eluting first with hexanes and then with 5% ethyl acetate in hexanes. The other fractions, from the first column containing intermediate 1-D, were slightly impure with a lower $R_f$ impurity. These fractions were combined, concentrated, and rechromatographed on silica gel, eluting with 10% ethyl acetate in hexanes. All the fractions containing intermediate 1-D were combined, concentrated, and dried in vacuo to give 624 mg (64%) of intermediate 1-D as a colorless, viscous oil. Thin layer chromatography: $R_f = 0.56$ (silica gel, 20% ethyl acetate in hexanes).

1-E. [1S-1α,3β,4aα,7β,8β(2S*,4S*),8a,β]-Decahydro-3-[(1,1-dimethylethyl)dimethylsilyl]oxy]-7-methyl-8-[2-(tetrahydro-4-[[(1,1-dimethylethyl)dimethylsilyl]oxy]-6-(1-methoxy-1-methylethoxy)-2H-pyran-2-yl)ethyl]-1-naphthalenol A solution of 591 mg (0.829 mmol) of intermediate 1-D in 12 mL of diethyl ether was added to a suspension of 230 mg (6.07 mmol, 7.3 eq) of lithium aluminum hydride in 15 mL diethyl ether (2×2 mL ethyl ether rinses were used for complete transfer of intermediate 1-D). After stirring for 1.25 hours at ambient temperature under argon, the reaction mixture was treated successively with water (0.230 mL), aqueous 20% sodium hydroxide (0.230 mL), and water (0.690 mL). After vigorously stirring for 1 hour, the mixture was filtered, washing with ethyl acetate. The filtrate was concentrated, and the crude product was chromatographed on silica gel, eluting with 7% ethyl acetate in hexanes. The purified product was isolated as a colorless, viscous oil in a yield of 489 mg (96%).

Thin layer chromatography: $R_f = 0.42$ (silica gel, 20% ethyl acetate in hexanes).

1-F [1S-[1α,3β,4aα,7β,8β(2S*,4S*),8a,β]-Octahydro-3-[[(1,1-dimethylethyl)dimethylsilyl]oxy]-7-methyl-8-[2-(tetrahydro-4-[[(1,1-dimethylethyl)dimethylsilyl]oxy]-6-(1-methoxy-1-methylethoxy)-2H-pyran-2-yl)ethyl]-1-(2H)-naphthalenone A solution of 450 mg (0.734 mmol) of intermediate 1-E in 3 mL of methylene chloride was added to a solution of Dess-Martin periodinane in 4 mL methylene chloride via a cannula (and 2×1 mL methylene chloride rinses were used for complete transfer of intermediate 1-E). After 30 minutes, the homogeneous reaction mixture was diluted with 60 mL of diethyl ether and poured into a solution of 0.850 g sodium thiosulfate (5.38 mmol, 7.3 eq) in 10 mL of aqueous sodium hydrogen carbonate. The two layers were stirred for 15 minutes, transferred to a separatory funnel, and separated. The ethyl ether layer was washed with 5 mL aqueous sodium hydrogen carbonate and 5 mL water, dried with magnesium sulfate, and concentrated. The product was purified by silica gel chromatography, eluting with hexanes (250 mL) and then 5% ethyl acetate in hexanes (250 mL) in a yield of 377 mg (82%) as a colorless, viscous oil.

Thin layer chromatography: $R_f = 0.53$ (silica gel, 20% ethyl acetate in hexanes).

1-G. [1S-[1α,3β,4aα,7β,8β(2S*,4S*),8a,β]-Decahydro-3-[[(1,1-dimethylethyl)dimethylsilyl]oxy]-1,7-dimethyl-8-[2-(tetrahydro-4-[[(1,1-dimethylethyl)dimethylsilyl]oxy]-6-(1-methoxy-1-methylethoxy)-2H-pyran-2-yl)ethyl]-1-naphthalenol To a solution of 1.5 g (2.39 mmol, 1.0 eq's) of decalone intermediate 1-F in 5 mL of dry tetrahydrofuran at 0° C. under an argon atmosphere was added 880 μL (2.63 mmol, 1.1 eq's) of a 3.0 M tetrahydrofuran solution of methyl magnesium bromide. The reaction was brought to ambient temperature for 30 minutes and stirred overnight (14 hours). The reaction was then diluted with 30 mL of ethyl acetate and quenched by addition of 20 mL of pH 4 buffer solution. The organics were separated, washed once with 20 mL of brine, dried with magnesium sulfate and concentrated in vacuo. The purified product was isolated by elution from silica gel, with an initial eluent of 5% ethyl acetate in hexanes followed by 10% ethyl acetate in hexanes, in a yield of 1.06 g (68.8%) as a nearly colorless, clear oil.

Thin layer chromatography: $R_f = 0.34$ (silica gel; 15 ethyl acetate in hexanes).

1-H. [1S-[1α,3β,4aα,7β, 8β(2S*,4S*),8a,β]-Decahydro-3-[[(1,1-dimethylethyl)dimethylsilyl]oxy]-1,7-dimethyl-8-[2-(tetrahydro-4-[[(1,1-dimethylethyl)dimethylsilyl]oxy]-6-hydroxy-2H-pyran-2-yl)ethyl]-1-naphthalenol A solution of 572 mg (0.89 mmol, 1.0 eq's) of methoxymethylethyl mixed acetal intermediate 1-G in 1.5 mL of tetrahydrofuran, 0.5 mL of water and 0.5 mL of acetic acid was stirred at ambient temperature for a period of 2.5 hours. This mixture was then diluted with ether, treated with 7 mL of water and made basic by cautious addition of solid sodium hydrogen carbonate. The organics were separated, washed once with brine, dried quickly with magnesium sulfate (e.g., 2 minute contact time), concentrated in vacuo and subjected to silica gel chromatography. The purified product was eluted with 50% ethyl acetate in hexanes following ca. 10 column volumes of a 5 to 10% ethyl acetate in hexanes gradient system in a yield of 467 mg (92%) as a nearly colorless, viscous oil. A mixture of lactol isomers was obvious from both the thin layer chromatography and $^1$H NMR analysis. Thin layer chromatography: $R_f$=0.2 (silica gel; 20% ethyl acetate in hexanes).

1-I. [1S-[1α,3β,4aα,7β,8β(2S*,4S*),8a,β]-Decahydro-3-[[(1,1-dimethylethyl)dimethylsilyl]oxy]-1,7-dimethyl-8-[2-(tetrahydro-4-[(1,1-dimethylethyl)dimethylsilyl]oxy]-6-oxo-2H-pyran-2-yl)ethyl]-1-naphthalenyl ester To a solution of 440 mg (0.77 mmol, 1.0 eq's) of lactol intermediate I in 2 mL of dry acetone (prepared by stirring acetone over magnesium sulfate for 15 minutes immediately prior to use) was added ca. 200 mg of freshly activated 4Å molecular sieves (powdered) and 185 mg of N-methylmorpholine-N-oxide. This mixture was stirred for 30 minutes prior to the addition of 20 mg of tris (triphenylphosphine)ruthenium (II) chloride. After a 30- minute reaction period, the mixture was filtered through a pad of Celite® with an exhaustive ethyl acetate rinse and concentrated in vacuo. The product was isolated as a viscous, clear and colorless oil, in pure form, via elution from a silica gel column with 40 to 50% ethyl acetate in hexanes with a yield of 436 mg (99.5%). Thin layer chromatography: $R_f$=0.59 (silica gel; 40% ethyl acetate in hexanes). 1-J. [1S-[1α,4β,7β,8β(2S*,4S*),8a,β]-2,2-Dimethylbutanoic acid, decahydro-3-[[(1,1-dimethylethyl)dimethylsilyl]oxy]-1,7-dimethyl-8-[2-(tetrahydro-4-[[(1,1-dimethylethyl)dimethylsilyl]oxy]-6-oxo-2H-pyran-2-yl)ethyl]-1-naphthalenyl ester Combined and stirred for 30 minutes were 600 mg (6.85 mmol, 7.5 eq's) of lithium bromide (anhydrous) and 620 mg (4.57 mmol, 5.0 eq's) of 2,2-dimethylbutyryl chloride in 4 mL of anhydrous pyridine. To this was added 520 mg (0.91 mmol, 1.0 eq's) of alcohol intermediate 1-I predissolved in 1 mL of pyridine, with an additional 0.5 mL pyridine used as a rinse, and the mixture was heated to 80° C. for 16 hours. Although incomplete, the reaction was interrupted by transferring to a separatory funnel, diluting with 30 mL of ethyl acetate and sequential washing with brine (once), saturated copper sulfate (twice), brine (once), saturated sodium hydrogen carbonate (once) and finally brine. The organic solution was then dried (magnesium sulfate) and concentrated in vacuo. Silica gel chromatography (25% ethyl acetate in hexanes) provided 473 mg (77.5%; 94.7% based on recovered starting material) of intermediate 1-J as a clear and nearly colorless oil.

Thin layer chromatography: $R_f$=0.67 (Silica gel; 40% ethyl acetate in hexanes).

1-K. [1S-[1α,3β,7β,8β(2S*,4S*),8a,β]-2,2-Dimethylbutanoic acid, decahydro-3-hydroxy-1,7-dimethyl-8-[2-(tetrahydro-4-hydroxy-6-oxo-2H-pyran-2-yl)ethyl]-1-naphthalenyl ester To a solution of 473 mg (0.71 mmol) of bis-silyl ether intermediate 1-J in 2.5 mL of acetonitrile was added 750 μL of hydrogen fluoride pyridine complex. After 10 minutes, the mixture was diluted with 50 mL of ethyl acetate and washed sequentially with brine (once), saturated copper sulfate (twice), brine (once), saturated sodium hydrogen carbonate (once) and brine before drying (magnesium sulfate) and concentrating in vacuo. The purified product (Example 1) was isolated by recrystallization from a hot hexanes diethylether/ethyl acetate mixture in a yield of 150 mg (first crop) and 75 mg (second crop) (72.3% total) as a slightly colored crystalline solid with a melting point of 150° to 151.5° C.

Thin layer chromatography: $R_f$=0.28 (Silica gel; 100% ethyl acetate).

EXAMPLE 2

[1S-[1α(βS*,ΔS*)2α,4αβ,6α,8β,8aα]]-Decahydro-α,Δ, 6-trihydroxy-2,8-dimethyl-8-(2,2-dimethyl-1-oxobutoxy)-1-naphthaleneheptanoic acid, monosodium salt 500 mL (1.16 eq's) of 1.0 N sodium hydroxide solution was added in a slow, dropwise fashion to a mixture of 190 mg (0.43 mmol, 1.0 eq's) of hydroxylactone Example 1 in 1.75 mL of dioxane and 1.75 mL of water at ambient temperature. After 30 minutes, the reaction was concentrated to a volume of ca. 1.5 mL and subjected to purification of CHP-20P. The product (Example 2) was eluted with 25% acetonitrile in water following an initial rinse with water and isolated as a white, electrostatic lyophilate in a yield of 185 mg (89.4%).

Thin layer chromatography: $R_f$=0.13 (silica gel; 15:1:1 dichloromethane/methanol/acetic acid).

EXAMPLE 3

[1S-[1α,3β,7β,8β(2S*,4S*),8a,β]-2,2-Dimethylbutanoic acid,
decahydro-3-hydroxy-7-methyl-1-(2-propenyl)-8-[2-(tetrahydro-4-hydroxy-6-oxo-2H-pyran-2-yl)ethyl]-1-naphthalenyl ester 3-A. [1S-[1α,3β,4aα,7β,8β(2S*,4S*),8a,β]-Decahydro-3-[[(1,1-dimethylethyl)dimethylsilyl]oxy]-7-methyl-1-(2-propenyl)-8-2-(tetrahydro-4-[(1,1-dimethylethyl)dimethylsilyl]oxy]-6-(1-methoxy-1-methylethoxy)-2H-pyran-2-yl)ethyl]-1-naphthalenol To a solution of 1.61 g (2.57 mmol) of decalone intermediate 1-F in 20 mL of dry tetrahydrofuran at −78° C. under an argon atmosphere was added 2.82 mL (2.82 mmol) of a 1.0 M ethereal solution of allyl magnesium bromide in a dropwise fashion over 10 minutes. After stirring at −78° C. for 20 minutes, the reaction was nearly complete as determined by thin layer chromatography. The reaction was warmed to 0° C. for 45 minutes and ambient temperature for 30 minutes, during which time the reaction progresses only slightly. The solution was recooled to −78° C. and treated with two portions of 0.257 mL (0.257 mmol) of allyl magnesium bromide in diethyl ether, after which the reaction was complete. The reaction was diluted with ethyl acetate (75 mL) and quenched by the addition of aqueous ammonium chloride solution. The aqueous layer was separated and extracted with ethyl acetate (2×30 mL). The organic layers were combined, dried (sodium sulfate), and chromatographed on silica gel, eluting with 5% ethyl acetate in hexanes (200 mL) followed by 6% ethyl acetate in hexanes (400 mL). The product was isolated in a yield of 1.60 g (93%) as a colorless oil.

Thin layer chromatography: $R_f=0.48$ (Silica gel, 25% ethyl acetate in hexanes).

3-B.  [1S-[1α,3β,4aα,7β,8β(2S*,4S*),8a,β]-Decahydro-3-[[(1,1-dimethylethyl)dimethylsilyl]oxy]-7-methyl-1-(2-propenyl)-8-[2-(tetrahydro-4-[[(1,1-dimethylethyl)dimethylsilyl]oxy]-6-hydroxy-2H-pyran-2-yl)ethyl]-1-naphthalenol A solution of 829 mg of methoxymethylethyl mixed acetal intermediate 3-A in 3 mL tetrahydrofuran, 1.5 mL of acetic acid, and 0.75 mL of water was stirred at ambient temperature under argon for 1.25 hours. To this mixture was added 25 mL of diethyl ether and 5 mL of water. Aqueous sodium hydrogen carbonate solution was added until the aqueous layer was made basic. The aqueous layer was then separated and extracted with ether (three times). The organic layers were combined, dried (sodium sulfate), and concentrated. The residue was chromatographed on silica gel, eluting with 5% ethyl acetate in hexanes (250 mL), 10% ethyl acetate in hexanes (250 mL) and then 15% ethyl acetate in hexanes (350 mL). The product was isolated in a yield of 667 mg (90%) as a colorless oil.

Thin layer chromatography: $R_f=0.20$ to 0.34 (Silica gel, 25% ethyl acetate in hexanes).

3-C.  [1S-[1α,3β,4aα,7β,8β(2S*,4S*),8a,β]-Decahydro-3-[[(1,1-dimethylethyl)dimethylsily]oxy]-7-methyl-1-(2-propenyl)-8-[2(tetrahydro-4-[[(1,1-dimethylethyl)dimethylsilyl]oxy]-6-oxo-2H-pyran-2-yl)ethyl]-1-naphthalenol To a solution of 620 mg (1.04 mmol) of lactol intermediate 3-B in 10 mL of acetone (dried over magnesium sulfate prior to use) was added 400 mg of powdered 4Å molecular sieves (activated) and 243 mg of N-methylmorpholine-N-oxide. This mixture was stirred for 10 minutes and tris(triphenylphosphine)ruthenium(II) chloride was added. After 10 minutes, the mixture was diluted with ethyl acetate and filtered over Celite ®, washing with ethyl acetate. The filtrate was concentrated, and the residue was chromatographed on silica gel, eluting with 5% ethyl acetate in hexanes (100 mL), 10% ethyl acetate in hexanes (100 mL), and then 15% ethyl acetate in hexanes (300 mL). The fractions containing the desired product were combined, concentrated, and dried in vacuo, giving the product as a colorless oil in a yield of 609 mg (97%).

Thin layer chromatography: $R_f=0.29$ (Silica gel, 25% ethyl acetate in hexanes).

3-D.  [1S-[1α,3β,7β,8β(2S*,4S*),8a,β]-2,2-Dimethylbutanoic acid, decahydro-3-[[(1,1-dimethylethyl)dimethylsilyl]oxy]-7-methyl-1-(2-propenyl)-8-2-(tetrahydro-4-[[(1,1-dimethylethyl)dimethylsilyl]oxy]-6-oxo-2H-pyran-2-yl)ethyl]-1-naphthalenyl ester A mixture of 670 mg (7.7 mmol) of anhydrous lithium bromide (LiBr) in 4 ml pyridine and 789 µL (5.75 mmol) of 2,2-dimethylbutyryl chloride in 4 ml pyridine was stirred for 30 minutes at ambient temperature under argon. The mixture was warmed (50° C.) briefly for dissolution of the LiBr. This solution and 122 mg (0.958 mmol) of 4-dimethylaminopyridine was added to a solution of alcohol intermediate 3-C in 2 ml of pyridine. This solution was heated at 80° C. for 15 hours and at 90° C. for 10 hours. Since the reaction progresses only slightly over the last 10 hours, a small spatula tip of LiBr and 200 ml of 2,2-dimethylbutyryl chloride was added. After stirring for 24 hours at 90° C., the homogeneous reaction mixture was diluted with ethyl acetate and sequentially washed with brine (once), aqueous copper sulfate (twice), brine (twice), aqueous sodium hydrogen carbonate, and water. The ethyl acetate layer was dried over magnesium sulfate and concentrated in vacuo. The residue was chromatographed on silica gel, eluting with 2% ethyl acetate in hexanes (250 mL), 5% ethyl acetate in hexanes (500 mL), and then 10% ethyl acetate in hexanes (400 mL). The product was isolated in a yield of 474 mg (71%) as a pale yellow oil.

Thin layer chromatography: $R_f=0.44$ (Silica gel, 25% ethyl acetate in hexanes).

3-E.  [1S-[1α,3β,7β,8β(2S*,4S*),8a,β]-2,2-Dimethylbutanoic acid, decahydro-3-hydroxy-7-methyl-1-(2-propenyl)-8-2-(tetrahydro-4-hydroxy-6-oxo-2H-pyran-2-yl)ethyl]-1-naphthalenyl ester A solution of bis-silylether intermediate 3-D in 3.5 mL of acetonitrile at 0° C. under argon was treated with 0.5 mL portions of hydrogen fluoride-pyridine until complete reaction was observed. After the addition of three portions, the reaction was complete. The homogeneous reaction mixture was diluted with ethyl acetate and sequentially washed with aqueous copper sulfate solution (once), brine (twice), aqueous sodium hydrogen carbonate solution (twice), and brine (once). The ethyl acetate layer was dried (sodium sulfate) and concentrated in vacuo. Purification of silica gel column chromatography, eluting with 50% hexanes in ethyl acetate (200 mL) followed by 30% hexanes in ethyl acetate, gave the product in a yield of 283 mg (96%) as a nearly colorless oil.

Thin layer chromatography: $R_f=0.33$ (Silica gel, 100% ethyl acetate).

EXAMPLE 4

[1S-[1α(βS*,ΔS*)2α,4aβ,6α,8β,8aα]]-8-(2,2-Dimethyl-1-oxobutoxy)decahydro-6β,Δ,6-trihydroxy-2-methyl-8-(2-propenyl)-1-naphtaleneheptanoic acid, monosodium salt To a solution of hydroxylactone Example 3 in 6 ml dioxane at 0° C. under argon was added a 1.0 N solution of NaOH. The cooling bath was immediately removed. After 15 minutes, the homogeneous reaction mixture was concentrated, dissolved in a minimum amount of water, and chromatographed on HP-20, eluting with water (200 mL), 10% acetonitrile in water (200 mL), and then 20% acetonitrile in water (400 mL). The fractions containing the desired product was combined and concentrated in vacuo. The oily residue was dissolved in water, filtered (Millipore, silver nitrate) and concentrated to ca. 1 mL. The aqueous solution was freeze-dried to give 243 mg (85%) of the product as a white lyophilate.

Thin layer chromatography: $R_f=0.27$ (Silica gel, 20:1:1 dichloromethane:methanol:acetic acid).

The foregoing represent preferred embodiments of this invention. Other embodiments are possible, as will be apparent to those skilled in the art. The foregoing examples are illustrative rather than limiting; the scope of this invention is limited only by the claims appended hereto.

What is claimed is:

1. A compound of the formula

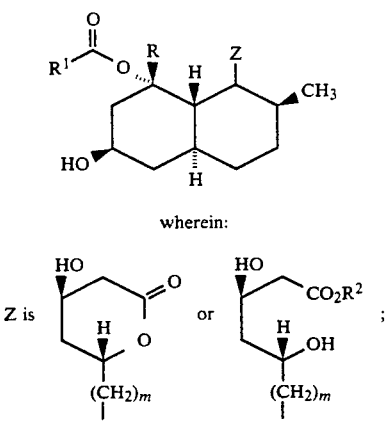

wherein:

R is selected, from:
(1) alkyl;
(2) substituted alkyl in which one or more substituents are selected from
 (a) hydroxyl,
 (b) alkoxy,
 (c) alkoxycarbonyl,
 (d) acyloxy,
 (e) cycloalkyl,
 (f) aryl,
 (g) substituted aryl having substituents X and Y, and
 (h) oxo;
(3) alkoxy;
(4) alkenyl;
(5) cycloalkyl;
(6) aryl; and
(7) substituted aryl having substituents X and Y;

$R^1$ is selected from:
(1) alkyl;
(2) substituted alkyl in which one or more substituents are selected from
 (a) halogen,
 (b) hydroxyl,
 (c) alkoxy,
 (d) alkoxycarbonyl,
 (e) acyloxy,
 (f) cycloalkyl,
 (g) aryl,
 (h) substituted aryl having substituents X and Y,
 (i) alkyl—$S(O)_n$,
 (j) cycloalkyl—$S(O)_n$,
 (k) aryl—$S(O)_n$,
 (l) substituted aryl—$S(O)_n$ having substituents X and Y, and
 (m) oxo;
(3) alkoxy;
(4) alkenyl;
(5) cycloalkyl;
(6) substituted cycloalkyl having a substituent selected from
 (a) alkyl,
 (b) substituent alkyl having a substituent selected from
  (i) halogen,
  (ii) hydroxy,
  (iii) alkoxy,
  (iv) alkoxycarbonyl,
  (v) acyloxy,
  (vi) aryl,
  (vii) substituted aryl having substituents X and Y,
  (viii) alkyl—$S(O)_n$,
  (ix) cycloalkyl—$S(O)_n$,
  (x) aryl—$S(O)_n$,
  (xi) substituted aryl—$S(O)_n$ having substituents X and Y, and
  (xii) oxo,
 (c) alkyl—$S(O)_n$,
 (d) cycloalkyl—$S(O)_n$,
 (e) aryl—$S(O)_n$,
 (f) substituted aryl—$S(O)_n$ in which the substituents are X and Y,
 (g) halogen,
 (h) hydroxy,
 (i) alkoxy,
 (j) alkoxycarbonyl,
 (k) acyloxy,
 (l) aryl, and
 (m) substituted aryl having substituents X and Y
(7) aryl;
(8) substituted aryl having substituents X and Y;
(9) amino;
(10) alkylamino;
(11) dialkylamino;
(12) arylamino;
(13) substituted arylamino having substituents X and Y;
(14) alkyl(substituted aryl)amino having substituents X and Y;
(15) diarylalkylamino;
(16) substituted arylalkylamino having substituents X and Y;
(17) a member selected from
 (a) piperidinyl,
 (b) pyrrolidinyl,
 (c) piperazinyl,
 (d) morpholinyl,
 (e) thiomorpholino,
 (f) histaminyl,
 (g) 3-aminomethyl pyridinyl; and
(18) hydroxy-substituted alkylamine;

$R^2$ is selected from:
(1) hydrogen;
(2) ammonium;
(3) alkali metal;
(4) alkyl;
(5) alkyl substituted with phenyl;
(6) dialkylamine;
(7) alkylarylamine; and
(8) diarylalkylamine;

X and Y are independently hydrogen, halogen, trifluoromethyl, alkyl, nitro, alkoxy, or cyano;
m is an integer from 0 to 3; and
n is 0, 1, or 2.

2. The compound of claim 1, wherein R is alkyl.
3. The compound of claim 1, wherein R is methyl.
4. The compound of claim 1, wherein R is alkenyl.
5. The compound of claim 1, wherein R is propenyl.
6. The compound claim 1, wherein $R^1$ is branched-chain alkyl.
7. The compound of claim 1, wherein $R^1$ is 1,1-dimethylpropyl.
8. The compound of claim 1, wherein Z is 9. The compound of claim 1, wherein

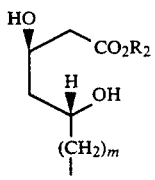

$R^2$ is alkali metal.

10. The compound of claim 1, wherein Z is

Z is 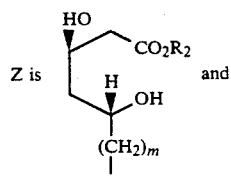 and 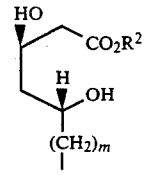

and $R^2$ is sodium.

11. The compounds of claim 1 having the names:
[1S-[1α,3β,7β,8β(2S*,4S*),8a,β]-2,2-dimethylbutanoic acid, decahydro-3-hydroxy-1,7-dimethyl-[2-(tetrahydro-4-hydroxy-6-oxo-2H-pyran-2-yl)ethyl]-1-naphthalenyl ester,

[1S-[1α(βS*,ΔS*)2α,4aβ,6α,8β,8aα]]-decahydro-α,Δ,6-trihydroxy-2,8-dimethyl-8-(2,2-dimethyl-1-oxobutoxy)-1-naphthaleneheptanoic acid, monosodium salt,

[1S-[1α,3β,7β,8β(2S*,4S*),8a,β]-2,2-dimethylbutanoic acid, decahydro-3-hydroxy-1-methyl-1-(2-propenyl)-8-[2-(tetrahydro-4-hydroxy-6-oxo-2H-pyran-2-yl)ethyl]-1-naphthalenyl ester, and

[1S-[1α(βS*,ΔS*)2α,4aβ,6α,8β,8aα]]-8-(2, 2-dimethyl-1-oxobutoxy)decahydro-β,Δ,6-trihydroxy-2-methyl-8-(2-propenyl)-1-naphthaleneheptanoic acid, monosodium salt.

12. A pharmaceutical composition having antihypercholesterolemic activity, which comprises an effective amount of a compound of claim 1 and an inert carrier therefor.

* * * * *